(12) United States Patent
Tijsma et al.

(10) Patent No.: US 9,433,636 B2
(45) Date of Patent: *Sep. 6, 2016

(54) PROTECTIVE GEL BASED ON CHITOSAN AND OXIDIZED POLYSACCHARIDE

(75) Inventors: Edze Jan Tijsma, Middelburg (NL); Maria Nieves Gonzalez, Alcorcon (ES); Erica M. TenBroek, Roseville, MN (US); Nancy Schaffhausen, Oosterhout (NL)

(73) Assignee: Medtronic, Inc., Minneapolis, MN (US)

( * ) Notice: Subject to any disclaimer, the term of this patent is extended or adjusted under 35 U.S.C. 154(b) by 272 days.

This patent is subject to a terminal disclaimer.

(21) Appl. No.: 12/429,141

(22) Filed: Apr. 23, 2009

(65) Prior Publication Data
US 2009/0270346 A1    Oct. 29, 2009

Related U.S. Application Data

(60) Provisional application No. 61/047,590, filed on Apr. 24, 2008.

(51) Int. Cl.
| | | |
|---|---|---|
| A01N 43/04 | (2006.01) |
| A61B 17/08 | (2006.01) |
| A61K 31/722 | (2006.01) |
| A61K 9/00 | (2006.01) |
| A61K 9/06 | (2006.01) |
| A61K 31/717 | (2006.01) |
| A61K 31/718 | (2006.01) |
| A61K 47/36 | (2006.01) |
| A61L 26/00 | (2006.01) |
| A61L 31/04 | (2006.01) |
| A61L 31/14 | (2006.01) |
| A61L 31/16 | (2006.01) |

(52) U.S. Cl.
CPC ........... *A61K 31/722* (2013.01); *A61K 9/0043* (2013.01); *A61K 9/06* (2013.01); *A61K 31/717* (2013.01); *A61K 31/718* (2013.01); *A61K 47/36* (2013.01); *A61L 26/008* (2013.01); *A61L 26/009* (2013.01); *A61L 26/0052* (2013.01); *A61L 26/0066* (2013.01); *A61L 31/041* (2013.01); *A61L 31/145* (2013.01); *A61L 31/148* (2013.01); *A61L 31/16* (2013.01); *A61L 2300/00* (2013.01)

(58) Field of Classification Search
None
See application file for complete search history.

(56) References Cited

U.S. PATENT DOCUMENTS

| | | |
|---|---|---|
| 3,184,385 A | 5/1965 | Anderson |
| 3,678,931 A | 7/1972 | Cohen |
| 3,914,214 A | 10/1975 | Trimnell et al. |
| 3,989,044 A | 11/1976 | Meierhoefer |
| 4,604,384 A | 8/1986 | Smith et al. |
| 4,659,700 A | 4/1987 | Jackson |
| 4,895,724 A | 1/1990 | Cardinal et al. |
| 4,960,413 A | 10/1990 | Sagar et al. |
| 4,983,385 A | 1/1991 | Hasegawa et al. |
| 5,308,546 A | 5/1994 | Hansen et al. |
| 5,312,324 A | 5/1994 | Walthour |
| 5,318,780 A | 6/1994 | Viegas et al. |
| 5,550,189 A | 8/1996 | Qin et al. |
| 5,623,064 A | 4/1997 | Vournakis et al. |
| 5,667,778 A | 9/1997 | Atala |
| 5,676,964 A | 10/1997 | Della Valle |
| 5,679,658 A | 10/1997 | Elson |
| 5,688,522 A | 11/1997 | Hardy |
| 5,723,144 A | 3/1998 | Hardy |
| 5,747,475 A | 5/1998 | Nordquist et al. |
| 5,770,712 A | 6/1998 | Roy |
| 5,820,608 A | 10/1998 | Luzio et al. |
| 5,840,341 A | 11/1998 | Watts et al. |
| 5,993,846 A | 11/1999 | Friedman et al. |
| 6,051,648 A | 4/2000 | Rhee et al. |
| 6,096,018 A | 8/2000 | Luzio et al. |
| 6,123,965 A | 9/2000 | Jacob et al. |
| 6,224,893 B1 | 5/2001 | Langer et al. |
| 6,290,712 B1 | 9/2001 | Nordquist et al. |
| 6,320,029 B1 | 11/2001 | Miekka et al. |
| 6,334,968 B1 | 1/2002 | Shapiro et al. |
| 6,342,251 B1 | 1/2002 | Illum et al. |
| 6,344,488 B1 | 2/2002 | Chenite et al. |
| 6,346,272 B1 | 2/2002 | Viegas et al. |
| 6,417,347 B1 | 7/2002 | Herrmann et al. |
| 6,458,889 B1 | 10/2002 | Trollsas et al. |
| 6,514,522 B2 | 2/2003 | Domb |
| 6,545,042 B2 | 4/2003 | Sung et al. |
| 6,566,406 B1 | 5/2003 | Pathak et al. |
| 6,599,627 B2 | 7/2003 | Yeo et al. |

(Continued)

FOREIGN PATENT DOCUMENTS

| | | |
|---|---|---|
| CA | 2 348 842 A1 | 5/2000 |
| CA | 2 574 232 | 1/2006 |

(Continued)

OTHER PUBLICATIONS

Kumar et al., Chem. Rev. 2004, 104, 6017-6084.*

(Continued)

*Primary Examiner* — Layla Berry
(74) *Attorney, Agent, or Firm* — IPLM Group, P.A.

(57) ABSTRACT

Bodily tissue and structures may be protected using a fluid layer containing a mixture of chitosan and oxidized polysaccharide. The mixture forms a protective gel layer via in situ crosslinking. Compared to crosslinking using a low molecular weight aldehyde such as glutaraldehyde or genipin, oxidized polysaccharides appear to provide faster gelation while avoiding the use of potentially less bioacceptable low molecular weight aldehydes.

21 Claims, 4 Drawing Sheets

(56) References Cited

U.S. PATENT DOCUMENTS

| | | | |
|---|---|---|---|
| 6,602,952 | B1 | 8/2003 | Bentley et al. |
| 6,632,423 | B2 | 10/2003 | Jafari et al. |
| 6,664,301 | B1 | 12/2003 | Kross |
| 6,706,690 | B2 | 3/2004 | Reich et al. |
| 6,719,987 | B2 | 4/2004 | Burrell et al. |
| 6,806,260 | B1 | 10/2004 | Hirofumi et al. |
| 6,809,085 | B1 | 10/2004 | Elson et al. |
| 6,835,389 | B1 | 12/2004 | Dohi et al. |
| 6,989,373 | B2 | 1/2006 | Des Rosiers |
| 6,991,652 | B2 | 1/2006 | Burg |
| 7,053,068 | B2 | 5/2006 | Prinz |
| 7,070,582 | B2 | 7/2006 | Freyman et al. |
| 7,087,249 | B2 | 8/2006 | Burrell et al. |
| 7,098,194 | B2 | 8/2006 | Chenite et al. |
| 7,125,860 | B1 | 10/2006 | Renier et al. |
| 7,195,675 | B2 | 3/2007 | Okazaki et al. |
| 7,229,966 | B2 | 6/2007 | Quay et al. |
| 7,354,600 | B1 | 4/2008 | Bernkop-Schnürch |
| 7,834,065 | B2 * | 11/2010 | Nakajima et al. ............ 523/111 |
| 2002/0042473 | A1 | 4/2002 | Trollsas et al. |
| 2002/0064580 | A1 * | 5/2002 | Gord et al. .................. 426/105 |
| 2002/0193812 | A1 | 12/2002 | Patel et al. |
| 2003/0073663 | A1 | 4/2003 | Wiseman et al. |
| 2004/0029855 | A1 | 2/2004 | Klaveness et al. |
| 2004/0127698 | A1 | 7/2004 | Tsai et al. |
| 2004/0137041 | A1 | 7/2004 | You et al. |
| 2004/0219117 | A1 | 11/2004 | Shibata |
| 2005/0002893 | A1 * | 1/2005 | Goldmann ................ 424/70.27 |
| 2005/0019404 | A1 | 1/2005 | Sung et al. |
| 2005/0069572 | A1 | 3/2005 | Williams et al. |
| 2005/0096282 | A1 | 5/2005 | Lewin et al. |
| 2005/0136122 | A1 | 6/2005 | Sadozai et al. |
| 2005/0176620 | A1 | 8/2005 | Prestwych et al. |
| 2005/0208122 | A1 | 9/2005 | Allen et al. |
| 2005/0238702 | A1 | 10/2005 | Ishihara et al. |
| 2006/0054634 | A1 | 3/2006 | Mekata |
| 2006/0134185 | A1 | 6/2006 | Odermatt et al. |
| 2006/0147539 | A1 | 7/2006 | Sung et al. |
| 2006/0172000 | A1 * | 8/2006 | Cullen et al. .................. 424/445 |
| 2006/0234871 | A1 * | 10/2006 | Dalrymple et al. .......... 507/211 |
| 2006/0292030 | A1 | 12/2006 | Odermatt et al. |
| 2007/0020314 | A1 | 1/2007 | Haro et al. |
| 2007/0031467 | A1 * | 2/2007 | Abrahams et al. ............ 424/423 |
| 2007/0031474 | A1 | 2/2007 | Tayot |
| 2007/0048291 | A1 | 3/2007 | Mang et al. |
| 2007/0066924 | A1 * | 3/2007 | Hopman et al. ................ 602/48 |
| 2007/0087059 | A1 | 4/2007 | Everaerts et al. |
| 2007/0098675 | A1 | 5/2007 | Elisseff et al. |
| 2007/0110788 | A1 | 5/2007 | Hissong et al. |
| 2007/0191963 | A1 | 8/2007 | Winterbottom et al. |
| 2007/0202142 | A1 | 8/2007 | Laugier et al. |
| 2007/0264310 | A1 | 11/2007 | Hissong et al. |
| 2008/0031854 | A1 | 2/2008 | Prestwich et al. |
| 2008/0069857 | A1 | 3/2008 | Yeo et al. |
| 2008/0075657 | A1 | 3/2008 | Abrahams |
| 2008/0317765 | A1 | 12/2008 | Izraeli et al. |
| 2008/0319101 | A1 | 12/2008 | Nakajima et al. |
| 2009/0005339 | A1 | 1/2009 | Scholz et al. |
| 2009/0016978 | A1 | 1/2009 | Courtois et al. |
| 2009/0041814 | A1 | 2/2009 | Nanbu |
| 2009/0062233 | A1 | 3/2009 | Ji et al. |
| 2010/0291055 | A1 * | 11/2010 | Athanasiadis et al. ...... 424/94.1 |

FOREIGN PATENT DOCUMENTS

| | | |
|---|---|---|
| CN | 1872351 A | 12/2006 |
| EP | 0 815 879 A2 | 1/1998 |
| EP | 1 228 771 A1 | 8/2002 |
| EP | 1 880 738 A1 | 1/2008 |
| FR | 2 889 449 A1 | 8/2005 |
| JP | H07-116241 | 9/1995 |
| JP | 2000-095678 | 4/2000 |
| JP | 2002-327338 | 11/2002 |
| JP | 2008-247975 | 10/2008 |
| JP | 2008-285611 | 11/2008 |
| WO | WO 92/16245 | 10/1992 |
| WO | WO 93/21906 | 11/1993 |
| WO | WO 96/14828 | 5/1996 |
| WO | WO 98/19718 | 5/1998 |
| WO | WO 98/31712 A2 | 7/1998 |
| WO | WO 99/01166 | 1/1999 |
| WO | WO 99/07416 | 2/1999 |
| WO | WO 00/40252 | 7/2000 |
| WO | WO 01/00246 A2 | 1/2001 |
| WO | WO 03/020771 A1 | 3/2003 |
| WO | WO 03/057274 A2 | 7/2003 |
| WO | WO 03/080135 A1 | 10/2003 |
| WO | WO 2004/026200 A | 4/2004 |
| WO | WO 2007/059390 A1 | 5/2007 |
| WO | WO 2007/071375 A | 6/2007 |
| WO | WO 2008/005671 A2 | 1/2008 |
| WO | WO 2008/008857 A | 1/2008 |
| WO | WO 2008/067655 A | 6/2008 |
| WO | WO 2008/097317 A | 8/2008 |
| WO | WO 2009/028965 A1 | 3/2009 |

OTHER PUBLICATIONS

Novamatrix, by FMC Biopolymer, retrieved from internet <<http://www.novamatrix.biz/Portals/novamatrix/Content/Docs/ProductDocs/chitosan_General_info.pdf>> on Jul. 5, 2012, published in 2011, 2 pages.*
WO 2006/080523, Aug. 3, 2006, machine translation.*
Vaiman et al. IMAJ, vol. 7, Sep. 2005, pp. 571-574.*
Liu, G. et al., "Synthesis and Characterization of Chitosan/Dextran-Based Hydrogels for Surgical Use", Macromol. Symp., 279, pp. 151-157, (2009).
Anonymous, "CHITOFLEX™—Surgical", Sep. 2007, 2 pages, retrieved from the Internet at: www.alltracel.com/Portals/1/ChitoFlex%20-%20Surgical%20Product%20Overview%20Brochure.pdf.
Szczubialka et al., "Novel drug carrier-Chitosan gel microspheres with covalently attached nicotinic acid", Journal of Controlled Release, Elsevier, vol. 16, No. 2, e13-e15, XP005794286 (2006).
Mwale Fackson et al., "Biological evaluation of chitosan salts cross-linked to genipin as a cell scaffold for disk tissue engineering", Tissue Engineering, vol. 11, No. 1-2, 130-140, XP002518499 (2005).
Athanasiadis, Theo et al., "Effects of a novel chitosan gel on mucosal wound healing following endoscopic sinus surgery in a sheep model of chronic rhinosinusitis", The Laryngoscope, vol. 118, No. 6, 1088-1094, XP002535403 (2008).
Bernkop-Schnürch, A., et al., "Improvement in the mucoadhesive properties of alginate by the covalent attachment of cysteine", Journal of Controlled Release, Elsevier, 71, 277-285 (2001).
Leitner et al., "Thiomers in noninvasive polypeptide delivery: in vitro and in vivo characterization of a polycarbophilcysteine/glutathione gel formulation for human growth hormone", J. Pharm. Sci, 93, 1682-1691 (2004).
Bromberg, "Intelligent Polyelectrolytes and Gels in Oral Drug Delivery" Department of Chemical Engineering, Massachusetts Institute of Technology, Cambridge, Massachusetts, U.S.A. in Current Pharmaceutical Biotechnology, 4, 339-349 (2003).
Prestwich et al., "3-D culture in synthetic extracellular matrices: New tissue models for drug toxicology and cancer drug delivery", Advances in Enzyme Regulation, Elsevier Ltd., 47, 196-207 (2007).
Kast et al., "Thiolated polymers-thiomers: development and in vitro evaluation of chitosan-thioglycolic acid conjugates", Biomaterials, Elsevier Science Publishers, 22, 2345-2352 (2001).
Fwu-Long et al., pH-sensitive behavior of two-component hydrogels composed of N,O-carboxymethal chitosan and alginate, J. Biomater, Sci. Polymer Edn., vol. 16, No. 11, 1333-1345 (2005).
Fwu-Long et al., Synthesis and characterization of biodegradable TPP/genipin co-crosslinked chitosan gel beads, Polymer, 44, 6521-6530 (2003).
Reyes et al., A Modified Chondroitin Sulfate Aldehyde Adhesive for Sealing Corneal Incisions, Investigative Ophthalmology & Visual Science, vol. 6, No. 4, 1247-1250 (Apr. 2005).

(56) References Cited

OTHER PUBLICATIONS

Mi et al., *Synthesis and Characterization of a Novel Chitosan-Based Network Prepared Using Naturally-Occurring Crosslinker*, J Polym Sci, Part A: Polym Chem, 38, 2804-2814 (2000).
Mi et al., *Synthesis and characterization of biodegradable TPP/genipin co-crosslinked chitosan gel beads*, Polymer, 44, 6521-30 (2003).
Roldo et al., *Mucoadhesive thiolated chitosans as platforms for oral controlled drug delivery: synthesis and in vitro evaluation*, European Journal of Pharmaceutics and Biopharmaceutics, 57, 115-121 (2004).
Krauland et al., *Viscoelastic Properties of a New in situ Gelling Thiolated Chitosan Conjugate*, Drug Development and Industrial Pharmacy, 31, 885-893 (2005).
Bernkop-Schntirch, *Thiomers: A new generation of mucoadhesive polymers*, Advanced Drug Delivery Reviews, 57, 1569-1582 (2005).
Bernkop-Schntirch et al., *Thiomers: Preparation and in vitro evaluation of a mucoadhesive nanoparticulate drug delivery system*, International journal of Pharmaceutics, 317, 76-81 (2006).
Weng et al., *Rheological Characterization of in Situ Crosslinkable Hydrogels Formulated from Oxidized Dextran and N-Carboxyethyl Chitosan*, Biomacromolecules, 8, 1109-1115 (2007).
Wang et al., *Multifunctional chondroitin sulphate for cartilage tissue-biomaterial integration*, nature materials, vol. 6, 385-392 (May 2007).
Aspden et al, *Chitosan as a Nasal Delivery System: The Effect of Chitosan on in Vitro and in Vivo Mucociliary Transport Rates in Human Turbinates and Volunteers*, J Pharm Sci, 86, 4, 509-513 (1997).
Costain et al., *Prevention of postsurgical adhesions with N, O-carboxymethyl chitosan: Examination of the most efficacious preparation and the effect of N, O-carboxymethyl chitosan on postsurgical healing*, Surgery, 121, 3, 314-319 (1997).
Hong et al., *Covalently crosslinked chitosan hydrogel: Properties of in vitro degradation and chondrocyte encapsulation*, Acta Biomaterialia, 3, 1, 23-31 (2007).
Park et al., *Crosslinked hydrogels for tympanic membrane repair*, Otolaryngology—Head and Neck Surgery, 135, 887-883 (2006).
Carlsson et al., *Immobilization of Urease by Thiol-Disulphide Interchange with Concomitant Purification*, Eur. J. Biochem, 44, 189-194 (1974).
Hoober et al., *Sulfhydiyl Oxidase from Egg White*, The Journal of Biological Chemistry, vol. 274, No. 32, Issue of Aug. 6, 22147-22150 (1999).
Barbucci et al., *Hyaluronic acid hydrogel in the treatment of osteoarthritis*, Biomaterials 23, 4503-4513 (2002).
Haugh, M.G. et al., "The effect of dehydrothermal treatment on the mechanical and structural properties of collagen-GAG scaffolds", Royal College of Surgeons in Ireland, Department of Anatomy, 23 pages, (2009).
Ringe, K. et al., "Nanoparticle Drug Delivery to the Brain", Encyclopedia of Nanoscience and Nanotechnology, vol. 7, pp. 91-104, (2004).
NovaMatrix Ultrapure Biopolymer Systems catalog and prices, 4 pages (Sep. 2011).
Higashiyama, Takanobu, "*Novel functions and applications of trehalose*", Pure Appl. Chem., vol. 74, No. 7, pp. 1263-1269 (2002).

Bernkop-Schnürch, A., et al., "*Thiolated polymers-thiomers: synthesis and* in vitro *evaluation of chitosan—2—iminothiolane conjugates*", International Journal of Pharmaceutics, vol. 260, Issue 2, (Jul. 24, 2003).
Wang, et. al, "The synthesis and characterization of novel bioadhesive material thiolated chitosan", Chemical Journal of Chinese Universities, No. 1, vol. 29, January, pp. 206-211 (2008).
Ex parte Robert S. Bray, Appeal No. 2011-013427 in U.S. Appl. No. 11/686,054 (BPAI, 2013).
Huang et al., "The Application and Development of New Crosslinking Agent Genipin in Biomedicine", Shanghai Biomedical Engineering Journal, No. 1, vol. 24, pp. 21-25 (2003).
"Definition of derivative", 2 pages, retrieved from Merriam-Webster online dictionary on Apr. 6, 2011 at: http://www.merriamwebster.com/dictionary/derivative.
Grillet et al., Polymer Gel Rheology and Adhesion, Rheology pp. 59-80 (2012).
Bernkop-Schnürch et al., Thiolated chitosans, European Journal of Pharmaceutical and Biopharmaceutics, 57, pp. 9-17 (2004).
Grabovac, Vjera et al., "Comparison of the mucoadhesive properties of various polymers", Advanced Drug Delivery Reviews, 57, pp. 1713-1723 (2005).
A Subramanian, HY Lin. (Crosslinked chitosan: Its physical properties and the effects of matrix stiffness on chondrocyte cell morphology and proliferation. Journal of Biomedical Research Part A, vol. 75A, Issue 3, pp. 742-753 (Aug. 18, 2005).
G. Sandri et al., "Mucoadhesive and penetration enhancement properties of three grades of hyaluronic acid using porcine buccal and vaginal tissue, Caco-2 cell lines, and rat jejunum." Journal of Pharmacy and Pharmacology, vol. 56, pp. 1083-1090 (2004).
Moura, M.J. et al., "Rheological study of genipin cross-linked chitosan hydrogels", Biomacromolecules, 8(12), pp. 3823-3829 (2007).
Woodworth, Bradford A. M.D., et al., *A gelatin-thrombin matrix for hemostasis after endoscopic sinus surgery*, American Journal of Otolaryngology-Head and Neck Surgery, 30, pp. 49-53 (2009).
Vaiman, Michael, M.D., PhD, et al., *Use of Fibrin Glue as a Hemostatic in Endoscopic Sinus Surgery*, Ann. Otol. Rhinol Laryngol. 114:, pp. 237-241 (2005).
Chandra, Rakesh K. M.D., et al., *Long-Term Effects of FloSeal™ Packing After Endoscopic Sinus Surgery*, American Journal of Rhinology, 19, 3, 240-244 (May-Jun. 2005).
EVICEL® Fibrin Sealant (Human), Manufacturer's Brochure, ETHICON, 3 pages (2015).
SURGIFLO® Hemostatic Matrix Kit, Manufacturer's Brochure, ETHICON, 3 pages (2015).
Floseal Hemostatic Matrix, Manufacturer's Brochure, Baxter, 2 pages (2015).
TISSEEL [Fibrin Sealant] Control Center, Manufacturer's Brochure, Baxter, 2 pages (2015).
Floseal Hemostatic Matrix, 10mL, Manufacturer's Brochure, 2 pages (Jul. 2014).
Kim, J.H. M.D. et al., "*Antiadhesive effect of the mixed solution of sodium hyaluronate and sodium carboxymethylcellulose after endoscopic sinus surgery*", American Journal of Rhinology, vol. 21, No. 1, pp. 95-99, additional copyright page (Jan.-Feb. 2007).
Struszczyk, H.J., et al., "Microcrystalline Chitosan. I. Preparation and Properties of Microcrystalline Chitosan", Journal of Applied Polymer Science, vol. 33, pp. 177-189 (1987).
Zhang, L., et al., "Structure and Control Release of Chitosan/Carboxymethyl Cellulose Microcapsules", Journal of Applied Polymer Science, vol. 82, pp. 584-592 (2001).

* cited by examiner

PROTECTIVE GEL BASED ON CHITOSAN AND OXIDIZED POLYSACCHARIDE

CROSS REFERENCE TO RELATED APPLICATION

This application claims priority from U.S. provisional application Ser. No. 61/047,590 filed Apr. 24, 2008, the disclosure of which is incorporated herein by reference.

FIELD OF THE INVENTION

This invention relates to polysaccharides and to materials for use in or on tissue and structures in the ears, nose, throat, limbs and spinal column.

BACKGROUND

Certain polysaccharide materials have been used for surgical repair or drug delivery. Documents relating to such materials include U.S. Pat. Nos. 6,514,522 (Domb) and 7,053,068 B2 (Prinz), U.S. Patent Application Publication Nos. US 2005/0176620 A1 (Prestwych et al.) and US 2005/0238702 A1 (Ishihara et al.), Canadian Patent Application No. 2 348 842 A1 (Bernkop-Schnürch), Published PCT Application Nos. WO 98/31712 A2 (B.F. Goodrich Co.), WO 01/00246 A2 (Bentley et al.) and WO 03/020771 A1 (Mucobiomer Biotechnologische Forschungs-und Entwicklungs GmbH), Mi et al., *Synthesis and Characterization of a Novel Chitosan-Based Network Prepared Using Naturally-Occurring Crosslinker*, J Polym Sci, Part A: Polym Chem, 38, 2804-2814 (2000), Mi et al., *Synthesis and characterization of biodegradable TPP/genipin co-crosslinked chitosan gel beads*, Polymer, 44, 6521-30 (2003), Roldo et al., *Mucoadhesive thiolated chitosans as platforms for oral controlled drug delivery: synthesis and in vitro evaluation*, European Journal of Pharmaceutics and Biopharmaceutics, 57, 115-121 (2004), Krauland et al., *Viscoelastic Properties of a New in situ Gelling Thiolated Chitosan Conjugate*, Drug Development And Industrial Pharmacy, 31, 885-893 (2005), Bernkop-Schnürch, *Thiomers: A new generation of mucoadhesive polymers*, Advanced Drug Delivery Reviews, 57, 1569-1582 (2005), Bernkop-Schnürch et al., *Thiomers: Preparation and in vitro evaluation of a mucoadhesive nanoparticulate drug delivery system*, International journal of Pharmaceutics, 317, 76-81 (2006) and Weng et al., *Rheological Characterization of in Situ Crosslinkable Hydrogels Formulated from Oxidized Dextran and N-Carboxyethyl Chitosan*, Biomacromolecules, 8, 1109-1115 (2007).

SUMMARY OF THE INVENTION

The present invention provides, in one aspect, a fluid layer atop a bodily tissue or structure, the layer comprising chitosan and oxidized polysaccharide in amounts sufficient to form a protective gel layer in situ. The protective gel layer may assist in returning an injured, inflamed or surgically repaired tissue surface to a normal state, e.g., through one or more healing mechanisms such as modulation of an inflammatory response, phagocytosis, mucosal remodeling, recilation or other full or partial restoration of normal function.

The present invention provides in another aspect a method for treating a bodily tissue or structure, which method comprises:

a) applying to such tissue a fluid layer containing a mixture of chitosan and an oxidized polysaccharide, and b) allowing the mixture to form a protective gel layer in situ.

The disclosed fluid layer desirably is spray applied, and packaged in a multicomponent spray dispenser. The disclosed method and layer are especially useful for treating mucosal tissues in the ears, nose or throat and openings, recesses, passageways or joints in the limbs or spinal column.

BRIEF DESCRIPTION OF THE DRAWING

Like reference symbols in the various figures of the drawing indicate like elements. The elements in the drawing are not to scale.

DETAILED DESCRIPTION

The following detailed description describes certain embodiments and is not to be taken in a limiting sense. All weights, amounts and ratios herein are by weight, unless otherwise specifically noted. The terms shown below have the following meanings:

The term "adhesion" refers to the sticking together of a body structure or prosthetic material to tissue, to the sticking together of tissue to tissue with which it is in intimate contact for extended periods, or to the formation of tissue that connects body structures, prosthetic materials or tissues to one another across a normally open space.

The term "antimicrobial" refers to an ability to cause greater than a 90% numeric reduction (viz., at least a 1-log order reduction) in a population of one or more of *Staphylococcus aureus, Pseudomonas aeruginosa, Streptococcus pneumonia, Haemophilus influenzae* or *Moraxella catarrhalis*.

The terms "attached" and "adhered" when used in reference to a bacterial biofilm and a surface mean that the biofilm is established on and at least partially coats or covers the surface, and has some resistance to removal from the surface. As the nature of this relationship is complex and poorly understood, no particular mechanism of attachment or adherence is intended by such usage.

The term "bacterial biofilm" means a community of bacteria attached to a surface, with the organisms in the community being contained within an extracellular polysaccharide (EPS) matrix produced by the bacteria.

The term "biocompatible" when used in reference to a substance means that the substance presents no significant deleterious or untoward effects upon the body.

The term "biodegradable" when used in reference to a substance means that the substance will degrade or erode in vivo to form smaller chemical or physical species. Such degradation process may be enzymatic, chemical or physical.

The term "bioresorbable" when used in reference to a substance means that the substance is capable of being absorbed by the body.

The term "cohesive" when used in reference to a liquid or gel means that the liquid or gel when placed on a level surface will tend to (but need not in all cases) stick to itself and form a unitary mass.

The term "comminuted" when used in reference to a particulate material means that the particles have been fractured and reduced in size by cutting, grinding, pulverizing, triturating or other particle fracturing process employing externally-applied force.

The term "conformal" when used in reference to a composition applied to tissue or other body structure means that the composition can form a substantially continuous layer over an area to which the composition has been applied.

The terms "detaching", "removing" and "disrupting" when used in reference to a bacterial biofilm attached or adhered to a surface mean that at least a significant amount of the biofilm initially present on the surface no longer is attached or adhered to the surface. No particular mechanism of detachment, removal or disruption is intended by such usage.

The term "fluid" when used in reference to a substance means that the substance is a liquid having a loss modulus (G") greater than its storage modulus (G') and a loss tangent (tan δ) greater than 1.

The term "gel" when used in reference to a substance means that the substance is deformable (viz., is not a solid), G" is less than G' and tan δ is less than 1.

The term "gelation" when used with respect to formation of a gel layer means the time at which G" equals G' and tan δ equals 1.

The term "hemostat" means a device or material which stops blood flow.

The term "hydrogel" when used in reference to a gel means that the gel is hydrophilic and contains water.

The term "hydrated" when used in reference to a device or substance means that the device or substance contains uniformly distributed chemically-bound water. A "fully hydrated" device or substance is incapable of taking up additional water of hydration. A "partially hydrated" device or substance is capable of taking up additional water of hydration.

The term "inner ear" means the semicircular canals and cochlea.

The term "middle ear" means the region defined by the tympanic membrane, interior structures such as the ossicular chain, the surrounding lining and bordering structures such as the mastoid.

The term "mucoadhesive" when used in reference to a device or substance means that the device or substance will adhere to the mucus covering epithelia.

The term "nasal or sinus cavities" refers to the various tissues defining the normally air-filled passages and chambers within the nose and sinus including but not limited to the nostrils or nares, the nasal concha or turbinates, the frontal, ethmoid, sphenoid and maxillary sinuses, the sinus ostia and the nasopharnyx.

The term "polysaccharide" includes derivatives of polysaccharides and modified polysaccharides, as well as derivatives of individual polysaccharide species and modified individual polysaccharide species. For example, the term "carboxymethylcellulose" includes carboxymethylcellulose derivatives and modified carboxymethylcelluloses, the term "chitosan" includes chitosan derivatives and modified chitosans, and the term "starch" includes starch derivatives and modified starches.

The term "protective" when used in reference to a layer of a composition atop tissue or other body structure means that the layer may assist in returning an injured, inflamed or surgically repaired tissue surface to a normal state, e.g., through one or more healing mechanisms such as modulation of an inflammatory response, phagocytosis, mucosal remodeling, reciliation or other full or partial restoration of normal function.

The term "residence time" when used in reference to a protective gel layer atop tissue or other body structure means the time period during which the gel layer or portion thereof remains in place in vivo under gross observation.

The term "solvating" means to form a solution or dispersion containing a solvent or other carrier within which a solute is dissolved or suspended.

The term "substantially collagen-free" means containing a sufficiently low amount of collagen so as not to pose a potential risk of transmission of or infection with bovine spongiform encephalopathy (BSE) or variant Creutzfeldt-Jakob disease (vCJD).

The term "thin" when used in reference to a protective layer atop tissue or other body structure means having an average thickness less than about two millimeters.

Figure 1:
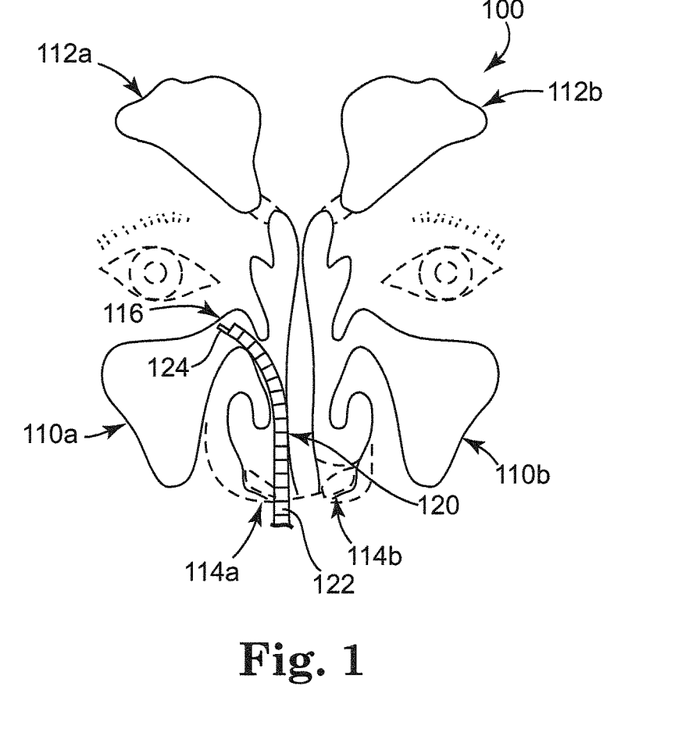
FIG. 1 is a schematic view showing the disclosed method.

Referring to FIG. 1, the disclosed method may be performed for example in the nasal or sinus cavities 100 of a patient, including the maxillary sinuses 110*a*, 110*b* and frontal sinuses 112*a*, 112*b*, which may be accessed through nares 114*a*, 114*b*. It should be noted that external features of the patient, including nares 114*a*, 114*b*, are shown in dashed lines. When the patient suffers for example from chronic rhinosinusitis, one or more treatment sites such as treatment site 116 associated with a surface of maxillary sinus 110*a* may be medically or if need be surgically addressed. Treatment site 116 includes ciliated epithelium of maxillary sinus 110*a* and may include an associated layer of bacteria inhabiting an associated biofilm (not shown in FIG. 1). The treatment site need not be natural tissue and may instead be an artificial structure (not shown in FIG. 1) such as a sinus packing or stent which may also be covered at least in part with a layer of bacterial biofilm. If present, the biofilm may be removed using a solvating system (for example, the solvating system described in U.S. Patent Application Publication No. US 2007/0264310 A1) which may be applied to treatment site 116 using an introducer 120 with an articulatable delivery tube 122 containing an irrigation duct (hidden in FIG. 1) through which the solvating system may flow to a nozzle 124 at the distal end of introducer 122 and thence to the treatment site. The solvating system and residues of the biofilm may be removed from the treatment site via an aspiration duct (hidden in FIG. 1). The disclosed composition comprising chitosan and oxidized polysaccharide may likewise be applied at the treatment site using the same or a different irrigation duct in introducer 120. Those skilled in the art will appreciate that the disclosed composition (and if used, the solvating system) may be applied to the treatment site using other methods or devices. Exemplary other methods include power spray or other spray application, lavage, misting, mopping, wicking, dripping and trephination and exemplary other devices include spray nozzles (e.g., single component or multiple component spraying nozzles) and syringes (e.g., single barrel or multiple barrel glass or plastic syringes and bulb syringes). The treatment method may also be performed in other parts of the body. The treatment method has particular utility in non-vascular applications, including treatment of tissues (e.g., mucosal tissues) or structures in or near the ears, throat, limbs or spinal column.

Figure 2:
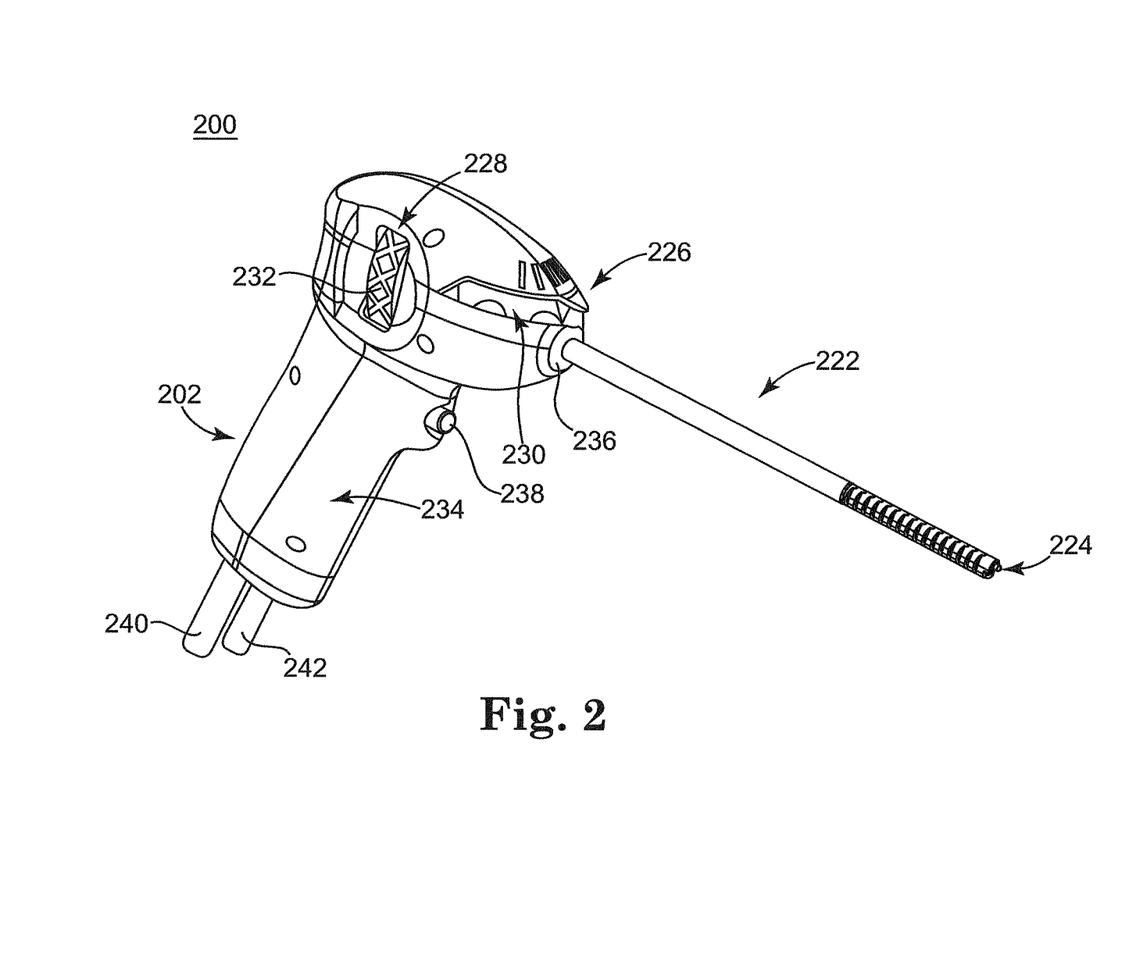
FIG. 2 is a perspective view of a dispensing instrument which may be used in the disclosed method.

FIG. 2 shows an exemplary instrument 200 which may be used in the disclosed treatment method. Instrument 200 includes a handle 202 and an introducer 222 whose distal end 224 (referenced generally) includes a spray nozzle, irrigation and aspiration ducts (not separately numbered in FIG. 2). Instrument 200 can optionally further include a first actuator assembly 226 (referenced generally) and a second actuator assembly 228 (referenced generally). A control wheel 230 in first actuator assembly 226 may be operable by a user to effectuate bending of the introducer 222, and a control wheel 232 in second actuator assembly 228 may be operable by a user to effectuate movement or rotation relative to introducer 222 of liquid sprayed from distal end 224 of introducer 222. Handle 202 serves generally as a housing for various other components of instrument 200 and as a support for introducer 222. Handle 202 may have a pistol grip-like shape, defining a grip portion 234 and a nose 236. Grip portion 234 is sized and shaped for grasping by a user's hand, whereas nose 236 is adapted for connection to introducer 222. Trigger 238 and an associated sensor and valve (not shown in FIG. 2) may be used to control the flow of the disclosed rehydrated gel (and if used, the disclosed solvating system) through irrigation tubing 240 and thence through the spray nozzle in distal end 224 and onto the desired treatment site. Trigger 238 may be provided with a multidirectional range of motion and associated with one or more additional sensors and valves (not shown in FIG. 2) to control removal from a treatment site of the solvating system, biofilm residue and other debris through the aspiration duct in distal end 224 and thence to aspiration tubing 242. Trigger 238 may also be used to control the flow of the disclosed rehydrated gel through a separate lumen in irrigation tubing 240 and thence through the spray nozzle in distal end 224 and onto the desired treatment site.

The applied composition comprising chitosan and oxidized polysaccharide may fill the treatment site (e.g., a nasal or sinus cavity, or an opening, recess, passageway or joint in a portion of the limbs or spinal column), in which case the disclosed layer of such composition may be very thick and not exposed to air or other nearby gases, and with differing thicknesses throughout the layer. The disclosed composition may also be applied as a thin film or other conformal coating in which case the disclosed layer may be relatively thin and exposed to air or other nearby gases, and with a substantially uniform thickness throughout the layer. After gelation the protective gel layer may be viscous, elastic or viscoelastic. The protective gel layer desirably adheres to mucosal or other natural tissues (e.g., cartilage or bone) at the treatment site and resists detachment or other disruption until natural degradation or resorption of the gel layer takes place, e.g., after a residence time in vivo of from one day to a few (e.g., 2, 3 or 4) days, weeks or months. Meanwhile bacterial recolonization or reinfection may be significantly reduced or prevented, and improved healing and reciliation may take place. The protective gel layer may provide various therapeutic advantages including but not limited to bacterial adhesion repellence, anti-infective properties, local immune modulation, tissue protection, reduction or elimination of pain or bleeding, reduction in inflammation, optimization of environment for ciliary regrowth, reduction in adhesions to critical anatomy, and the like. These advantages may arise due to a variety of mechanisms including a) killing bacteria, b) inhibiting bacterial colonization, c) inhibiting the adherence of bacteria to tissue, d) reducing tissue morbidity or abscess formation, e) reducing or preventing disease recurrence (for example, specifically reducing the chronic inflammation related to bacterial toxin and EPS), f) coating and protecting tissue during healing, such as by maintenance of a moist wound which promotes platelet aggregation, or by closure of a dry wound without excessive scabrous formation, g) hemostasis, h) optimizing the environment for reciliation of the mucosa, i) speeding the growth or regrowth of cilia and j) delivering therapeutic agent(s) to the treatment site. Desirably the protective gel layer will adhere to a portion of the mucosa while leaving the cilia in unadhered portions free to undergo natural rhythmic cilia motion (viz., cilia beating), will if desired also deliver antimicrobial agents or additional therapeutic agents, and desirably will discourage or prevent bacteria from adhering to the treatment site.

A wide variety of chitosans (including salts and other chitosan derivatives) may be employed in the disclosed fluid layer and method. Exemplary unmodified chitosans and their salts (including citrate, nitrate, lactate, phosphate, chloride and glutamate salts) may be obtained from a variety of commercial sources including KitoZyme S.A., Fluka Chemie AG, the NovaMatrix unit of FMC BioPolymer AS and Sigma-Aldrich Co. Chitosan may also be synthesized by deacetylation of chitin (poly-N-acetyl-D-glucosamine) to eliminate acetyl groups on the nitrogen atom by hydrolysis. The resulting polymer has a plurality of repeating units (e.g., about 30 to about 3000 repeating units, about 60 to about 600 repeating units, or such other amount as may be desired for the chosen end use) some or all of which contain deacetylated amino groups (e.g., about 30 to about 100% or about 60 to about 95% of the total repeating units), with the remaining repeating units (if any) containing acetylated amino groups. The polymer is cationic and may be regarded as being composed from glucosamine monomers. The chitosan may have a variety of number average molecular weights, e.g., about 5 to about 2000 kDa, about 10 to about 500 kDa, or about 10 to about 100 kDa. The chitosan may for example be an ultralow molecular weight material having a number average molecular weight less than about 50 kDa, a low molecular weight material having a number average molecular weight of about 50 to about 200 kDa, a medium molecular weight material having a number average molecular weight of about 200 to about 500 kDa or a high molecular weight material having a number average molecular weight greater than about 500 kDa. Chitosan derivatives may also be employed, for example derivatives in which one or more hydroxyl or amino groups have been modified for the purpose of altering the solubility or mucoadhesion characteristics of the derivative. Exemplary derivatives include thiolated chitosans, and non-thiolated chitosan derivatives such as acetylated, alkylated or sulfonated chitosans (for example O-alkyl ethers, O-acyl esters, cationized trimethyl chitosans and chitosans modified with polyethylene glycol). Chitosan derivatives may be obtained from a variety of sources. For example, thiolated chitosans may be obtained from ThioMatrix Forschungs Beratungs GmbH and Mucobiomer Biotechnologische Forschungs-und Entwicklungs GmbH or prepared by reaction of chitosan with a suitable thiolated reactant, e.g., as described in the above-mentioned Published PCT Application No. WO 03/020771 A1 or in the above-mentioned Roldo et al., Krauland et al., Bernkop-Schnürch and Bernkop-Schnürch et al. papers.

The chitosan desirably is obtained in dry particulate form, for example, as free-flowing granules whose average particle diameter is less than about 1 mm, less than about 100 µm, about 1 to about 80 µm, or less than 1 µm. The chitosan preferably is packaged and shipped to a user in such dry particulate form so as to reduce degradation of the chitosan during prolonged storage. The chitosan fluid may be formed for example by dissolving the chitosan in water or another suitable solvent just prior to use. Recommended chitosan amounts will depend on the chitosan molecular weight, and may for example be about 1 to about 20%, about 1 to about 10% or about 1 to about 5% of the resulting solution. Copending U.S. Provisional Application Ser. No. 61/047, 580, filed Apr. 24, 2008, describes a preferred technique for rehydrating a chitosan, by dispersing free-flowing chitosan particles in a biocompatible water-miscible polar dispersant, and combining the dispersion with sufficient aqueous solvent for the particles to convert them to a cohesive hydrogel. The chitosan may be comminuted but desirably is non-comminuted.

A wide variety of oxidized polysaccharides may be employed in the disclosed fluid layer and method. Exemplary polysaccharides include agars, alginates, carrageenans, celluloses, chitins, chitosan (thus enabling chitosan to be crosslinked using its oxidized counterpart), chondroitin sulfates, dextrans, galactomannans, glycogens, hyaluronic acids, starches and other biocompatible polysaccharides capable of being oxidized. Oxidized polysaccharides such as oxidized cellulose, chitin, chitosan, chondroitin sulfate, dextran, glycogen, hyaluronic acid and starch are preferred. The polysaccharide desirably is oxidized to an extent sufficient to provide aldehyde groups capable of promoting rapid crosslinking of the chitosan when the chitosan and oxidized polysaccharide are combined in aqueous solution. Representative oxidizing agents or techniques include the use of a) sodium periodate, b) hypochlorite ion in the presence of di-tert-alkylnitroxyl catalysts, c) metal-catalyzed oxidation, using for example ruthenium, d) anhydrous oxidation using for example nitrogen dioxide in for example a halocarbon, e) enzymatic or chemo-enzymatic oxidation of starch, guar and other polysaccharides, and other oxidation agents and techniques that will be known to persons having ordinary skill in the art. Depending on the selected oxidizing agent or technique, a variety of degrees of oxidation, degrees of polymerization and oxidation sites may be employed. For example, oxidation may be directed at a primary hydroxyl group (for example, the 6-hydroxyl group in the anhydroglucose units of glucans), resulting in carboxyl-polysaccharides with preserved ring structures. Oxidation may also be directed at a vicinal diol function present in a monosaccharide ring (for example, the C2-C3 site in anhydroglucose units), resulting in cleavage of the monosaccharide units and the production of dialdehyde or dicarboxyl functional groups. The dialdehyde content of such an oxidized polysaccharide may range from a degree of oxidation of, for example, 2% to virtually 100%, e.g., more than 30% or more than 50% of the available oxidation sites. The oxidized polysaccharide may also contain other functional groups, for example hydroxyalkyl groups, cationic groups, carboxyl groups and other acid groups. As a generalization, reduced amounts of oxidized polysaccharide may be employed in the disclosed fluid layer and method as the degree of polysaccharide oxidation is increased.

The oxidized polysaccharide desirably is dissolved in water or another suitable solvent prior to use. Recommended oxidized polysaccharide amounts typically will depend on the oxidized polysaccharide molecular weight, and may for example be about 1 to about 20%, about 1 to about 10% or about 1 to about 5% of the resulting solution. The oxidized polysaccharide solution normally is kept separate from the chitosan solution until just prior to use.

Compared to crosslinking using a low molecular weight aldehyde such as glutaraldehyde or genipin, oxidized polysaccharides appear to provide faster gelation while avoiding the use of potentially less bioacceptable low molecular weight aldehydes. In addition to their ability to react with amine groups in the chitosan, aldehyde groups in the oxidized polysaccharide may also enhance mucoadhesion. The oxidized polysaccharides may provide additional benefits including improved or better controlled biodegradability, bioresorbability, drug delivery or haemostatic properties. The presence of phosphate ions appears to accelerate the crosslinking reaction. Phosphate may be provided by using phosphate buffered saline (PBS) as a solvent for one or both of the chitosan and oxidized polysaccharide.

Sufficient chitosan and oxidized polysaccharide desirably are employed so that a protective gel layer will form in less than 30 minutes after the chitosan and oxidized polysaccharide are mixed, and more preferably in less than 20 minutes, less than 10 minutes, less than 5 minutes or essentially immediately after mixing. The resulting fluid mixture may for example contain chitosan and oxidized polysaccharide in a combined amount representing about 1 to about 20%, about 1 to about 10% or about 1 to about 5% of the composition. The chitosan and oxidized polysaccharide may for example be combined in a ratio of about 10:1 to about 1:20, about 5:1 to about 1:10, or about 3:1 to about 1:5. These ratios depend on the degree of oxidation of the oxidized polysaccharide(s), with lower oxidized polysaccharide amounts generally being used when more highly-oxidized polysaccharides are employed. For some applications the chitosan amount will preferably be as high as may be feasible in order to provide good antimicrobial properties, and in such cases it will be preferable to use a low amount of highly oxidized polysaccharide so as to obtain rapid gel formation.

The disclosed compositions desirably are substantially collagen-free. Preferably the compositions are sufficiently free of collagen (e.g., containing no collagen at all) so as to be saleable worldwide for use without restriction in humans.

The disclosed compositions may optionally include a variety of other ingredients. These other ingredients may be disposed before mixing in the first part, second part or both parts of a two-part composition. Exemplary other ingredients include water and other solvents (e.g., alcohols), acids, bases, buffering agents, antimicrobial agents, therapeutic agents and other adjuvants. An acid, base or buffering agent may for example maintain the composition at an appropriate pH for contacting human tissue, e.g., a pH greater than 5, a near-neutral pH, or a pH less than 8.5. Exemplary buffering agents include barbitone sodium, glycinamide, glycine, potassium chloride, potassium phosphate, potassium hydrogen phthalate, sodium acetate, sodium citrate, sodium phosphate and their conjugate acids.

The disclosed compositions desirably are inherently antimicrobial without requiring addition of a separate antimicrobial agent. Antimicrobial activity may be influenced by the proportion of chitosan in the composition (with higher chitosan proportions tending to provide greater antimicrobial activity) and by the number of available chitosan amine hydrogen atoms. Accordingly, use of chitosan derivatives containing low numbers of available amino hydrogen atoms (such as the N-carboxyethyl derivatives desired in the above-mentioned Weng et al. paper) may be contraindicated.

In any event, a separate antimicrobial agent may be employed if desired. A useful list of such antimicrobial agents may be found, for example, in the above-mentioned U.S. Patent Application Publication No. US 2007/0264310 A1.

Exemplary therapeutic agents which may be employed in the disclosed compositions include any material suitable for use at the intended treatment site including analgesics, anti-cholinergics, anti-fungal agents, antihistamines, steroidal or non-steroidal anti-inflammatory agents, anti-parasitic agents, antiviral agents, biostatic compositions, chemotherapeutic/antineoplastic agents, cytokines, decongestants, hemostatic agents (e.g., thrombin), immunosuppressors, mucolytics, nucleic acids, peptides, proteins, steroids, vasoconstrictors, vitamins, mixtures thereof, and other therapeutic materials that will be known to those skilled in the art. A useful list of such therapeutic agents may be found, for example, in the above-mentioned U.S. Patent Application Publication No. US 2007/0264310 A1.

Other adjuvants that may be included in the disclosed compositions include dyes, pigments or other colorants (e.g., FD & C Red No. 3, FD & C Red No. 20, FD & C Yellow No. 6, FD & C Blue No.2, D & C Green No. 5, D & C Orange No. 4, D & C Red No. 8, caramel, titanium dioxide, fruit or vegetable colorants such as beet powder or beta-carotene, turmeric, paprika and other materials that will be known to those skilled in the art); indicators; flavoring or sweetening agents including but not limited to anise oil, cherry, cinnamon oil, citrus oil (e.g., lemon, lime or orange oil), cocoa, eucalyptus, herbal aromatics (e.g., clove oil, sage oil or cassia oil), lactose, maltose, menthol, peppermint oil, saccharine, sodium cyclamate, spearmint oil, sorbitol, sucrose, vanillin, wintergreen oil, xylitol and mixtures thereof; antioxidants; antifoam agents; and rheology modifiers including thickeners and thixotropes. The disclosed compositions desirably do not contain ingredients which might potentially harm mucosal tissues or structures, e.g., tissues in the nasal or sinus cavities.

In those instances where it is desirable to remove water from tissue, e.g., to remove fluid from polyps or edematous tissue, a hyperosmolar agent may be employed in the disclosed compositions. Exemplary hyperosmolar agents include furosemide, sodium chloride gel and other salt preparations that draw water from tissue or substances which directly or indirectly change the osmolar content of the mucous layer. Where sustained release or delayed release of a therapeutic agent is desirable, a release agent modifier may also be included.

The disclosed composition typically will be subjected to sterilization and placed in suitable sealed packaging (for example, a multicomponent syringe, a vial or vials, or a multi-chamber pouch made of suitable materials) prior to shipment to an end user. Additional property customization may be carried out by using a sterilization procedure such as gamma radiation or electron beam (E-Beam) processing to cause controlled chain scission. Cold ionizing radiation sterilization (e.g., cold E-Beam sterilization) may be employed to limit the degree of chain scission, as discussed in PCT Application No. (Attorney Docket Nos. P0035142.00 and 151-P-35142WO01), filed even date herewith. Whether or not sterilized, the first part containing the chitosan normally will be kept separate from the second part containing the oxidized polysaccharide until just prior to use.

The disclosed compositions may desirably be used as a part of a multi-step treatment regimen which disrupts a bacterial biofilm and discourages its return. For example, a series of steps that may be broadly classified as Cleansing/Disrupting, Killing, Aerating, Protecting/Coating, and Healing may be carried out. The Cleansing/Disrupting step may be carried out by administering a solvating system as discussed above in connection with FIG. 1 and FIG. 2. The Killing step may be carried out by applying a suitable antimicrobial agent to the treatment site. This may for example be accomplished by including an antimicrobial agent in the solvating system, as a separately-applied composition, or in both the solvating system and in a separately-applied composition. An antimicrobial agent may also be applied or administered post operatively. The Aerating step may be carried out by providing air passageways or improving air passageways to the treated tissues by opening occluded or partially occluded passages, e.g., the sinuses or sinus ostia for nasal applications. This may for example be accomplished by surgically removing obstructive tissue structures or by manually displacing such structures. The Protecting/Coating step may be carried out by coating at least part of the thus-treated tissue with the disclosed composition containing chitosan and oxidized polysaccharide as described above. The Healing step may be carried out by allowing the cleansed, protected and sealed tissue surface to undergo a return to a normal state, e.g., through one or more healing mechanisms such as modulation of an inflammatory response, phagocytosis, mucosal remodeling, reciliation or full or partial restoration of normal function. The multi-step treatment regimen may include or be followed by a Clearing step in which the disclosed composition containing chitosan and oxidized polysaccharide is sufficiently biodegradable or bioresorbable to disappear from the treatment site in a desired time period, e.g., more than 1 day, more than 3 days, or about 4 to 7 days, and desirably without shedding large solid chunks. The disclosed method may advantageously be accomplished without requiring surgery, for example by applying and removing the optional solvating system and by applying the disclosed composition containing chitosan and oxidized polysaccharide through normal aspiration/suction techniques or by simple flushing of affected tissue. A comparable series of steps may be performed in a multi-step treatment regimen in a portion of the middle or inner ear. Further details regarding such a regimen may be found in U.S. Patent Application Publication No. US 2007/0264310 A1.

The invention is further illustrated in the following non-limiting examples.

EXAMPLE 1

Gel Formulations

Chitosan solutions were prepared by dissolving varying amounts of chitosan glutamate (PROTASAN™ UP G 113 or PROTASAN UP G 213 from the NovaMatrix unit of FMC BioPolymer AS) overnight in PBS. An oxidized starch (OXST) solution was prepared by dissolving P9265 polymeric dialdehyde (from Sigma-Aldrich) in PBS while heating at 80° C. for 1-2 hours. Oxidized methylcellulose (MC) and oxidized hydroxypropylmethylcellulose (HPMC) solutions were prepared by reacting MC or HPMC with sodium periodate, lyophilizing the resulting products, and dissolving the lyophilized products in PBS. The resulting chitosan solutions and oxidized polysaccharide solutions were mixed in various ratios and concentrations. Rheological measurements determined the gelling time and storage modulus (G') for the resulting hydrogels. The results are shown below in Table 1.

TABLE 1

Gelation Time and Storage Modulus G'

| Run No. | Chitosan | Oxidized Polysaccharide | Chitosan:Oxidized Polysaccharide Ratio | Total Conc. (%) | Gel time (min) | G' (Pa) |
|---|---|---|---|---|---|---|
| 1 | G 113 | OXST | 2:1 | 5 | <2[1] | 5,200 |
| 2 | G 113 | OXST | 1:1 | 5 | <2[1] | 4,000 |
| 3 | G 113 | OXST | 1:2 | 5 | <2[1] | |
| 4 | G 113 | OXST | 2:1 | 3.75 | <2[1] | 800 |
| 5 | G 113 | OXST | 1:1 | 3.33 | 3.2 | 400 |
| 6 | G 113 | OXST | 1:2 | 3 | 6.4 | 200 |
| 7 | G 213 | OXST | 2:1 | 2.5 | <2[1] | 750 |
| 8 | G 213 | OXST | 1:1 | 2.5 | <2[1] | 450 |
| 9 | G 113 | Oxidized MC | 1:2 | 7.5 | <1 day | |
| 10 | G 113 | Oxidized MC | 1:10 | 5 | <2[1] | |
| 11 | G 113 | Oxidized MC | 1:5 | 5 | <2[1] | 100 |
| 12 | G 113 | Oxidized MC | 1:1 | 5 | <1 day | |
| 13 | G 113 | Oxidized MC | 5:1 | 5 | no gelling | |
| 14 | G 113 | Oxidized HPMC | 1:4 | 12.5 | <60 | |
| 15 | G 113 | Oxidized HPMC | 1:2 | 7.5 | <1 day | |
| 16 | G 113 | Oxidized HPMC | 1:1 | 5 | no gelling | |

[1]Gelled before the rheometer measurement started

Each of the chitosan/oxidized polysaccharide formulations shown in Table 1 had a viscosity below 500 cP, and should be injectable at a mucosal tissue treatment site using for example a device like that shown in FIG. 2 or a variety of other devices that will be known to persons having ordinary skill in the art. The formulations shown in Table 1 should also be sprayable onto a mucosal treatment site. Due to the rapidity with which gelation occurred for some formulations, spray application would in many instances be a preferred mode of application. The Run No. 2 formulation (G 113 Chitosan/OXST 1:1 at a total concentration of 5%) was spray-applied using a gas-assisted applicator (Fibrijet™ SA-6030 regulator, from Micromedics, Inc., controlling a FibriJet SA-3652 spray set equipped with a pair of 3 cc syringes). The OXST solution was dyed using toluidine blue to make the applied fluid layer easier to see. A thin, rapidly formed strong gel was obtained.

EXAMPLE 2

Antimicrobial Properties

Figure 3:
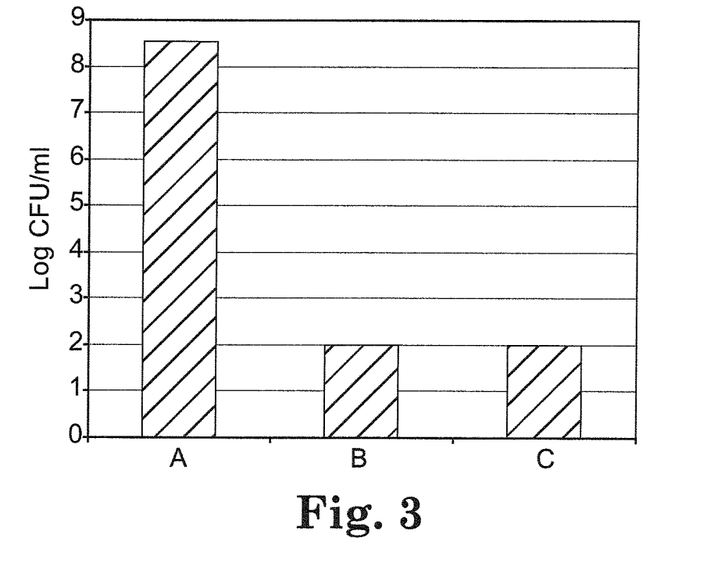
FIG. 3 is a graph showing the antimicrobial properties of two in situ crosslinked gel layers formed from chitosan and oxidized polysaccharide, and of a trypticase soy broth control.

The Run No. 7 and 8 formulations from Table 1 (G 213 Chitosan/OXST 2:1 and 1:1 at a total concentration of 2.5%, respectively shown as bars B and C in FIG. 3) were evaluated to determine their antimicrobial activity versus *S. Aureus*, using a plate procedure whose detection limit was log 2. The gel formulations were placed in duplicate under sterile conditions directly into a 24-well polystyrene tissue culture plate. Each well was incubated with 1 mL (25,000 colony forming units) of a bacterial suspension of *S. Aureus* (ATCC 25923). Positive controls were incubated with 1 ml of trypticase soy broth (TSB). After 6 hours incubation at 37° C., the media was transferred in new tubes and serial ten-fold dilutions were performed. Ten µL aliquots from the appropriate dilution were plated in triplicate on trypticase soy agar plates using the dilution track method (Jett B. D. et al., Biotechniques, 23, 648-650 (1997). The plates were incubated at 37° C. for 24 hours and Colony Forming Units (CFU) were counted. As shown in FIG. 3, both formulations exhibited complete (greater than 6 log reduction) killing of the bacteria vs. the TSB control (see bar A in FIG. 3).

Figure 4:
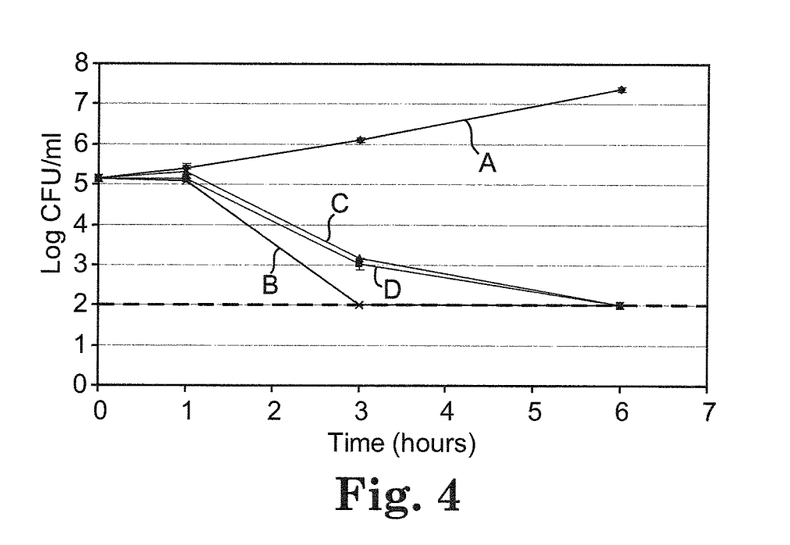
FIG. 4 is a graph showing antimicrobial activity as a function of time for three in situ crosslinked gel layers formed from chitosan and oxidized polysaccharide, and for a trypticase soy broth control.

The Run Nos. 2, 10 and 11 formulations from Table 1 (G 113 Chitosan/OXST 1:1, G 113 Chitosan/Oxidized MC 1:10 and G 113 Chitosan/Oxidized MC 1:5 at a total concentration of 5%, respectively shown as curves B, C and D in FIG. 4) were evaluated as described above to determine their antimicrobial activity as a function of time versus *S. Aureus*, using a 140,000 CFU/mL bacterial loading, with measurements being recorded at 1, 3 and 6 hours against a TSB control (see curve A in FIG. 4). As shown in FIG. 4, complete killing was observed after 6 hours for gels made from all three chitosan/oxidized polysaccharide formulations, with significant killing being observed after 3 hours. The G 113 Chitosan/OXST formulation appeared to provide faster killing than the G 113 Chitosan/Oxidized MC formulations.

EXAMPLE 3

Drug Delivery

Figure 5:
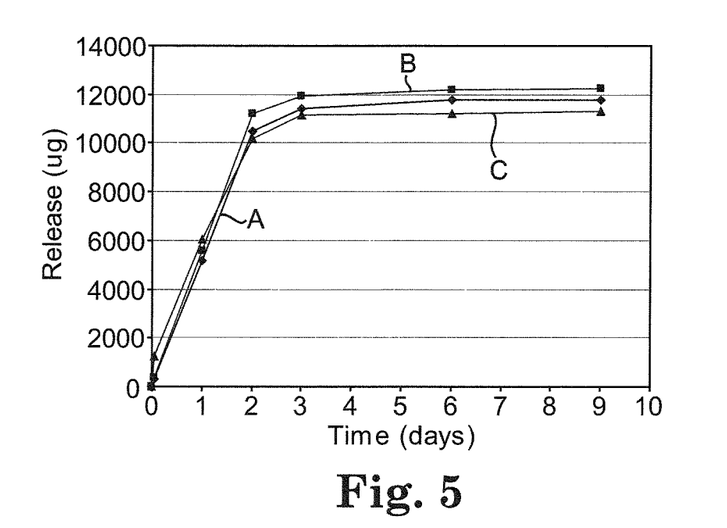
FIG. 5 is a graph showing drug release behavior for three in situ crosslinked gel layers.

The Run No. 1, 2 and 3 formulations from Table 1 (G 113 Chitosan/OXST 2:1, 1:1 and 1:2 at a total concentration of 5%, respectively shown as curves A, B and C in FIG. 5) were used to prepare drug-loaded hydrogels in PBS buffer by mixing the chitosan and oxidized starch solutions with dexamethasone phosphate as the drug to be delivered. As shown in FIG. 5, relatively fast but controlled release for up to 3 days was obtained for dexamethasone phosphate, possibly aided by an interaction between the anionic drug and the cationic chitosan polymer.

EXAMPLE 4

Degradation

Figure 6:
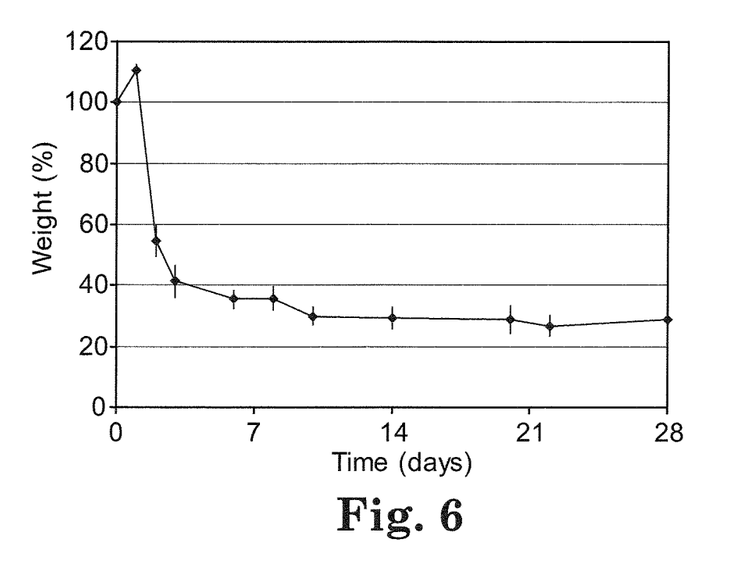
FIG. 6 is a graph showing degradation of an in situ crosslinked gel layer.

The degradation behavior of various chitosan/oxidized polysaccharide gel formulations was determined by placing the gels in various buffer systems, including PBS at pH 7.4 with and without lysozyme (1 mg/mL), PBS with lipase, 2-(N-morpholino)ethanesulfonic acid (MES) at pH 6.0, and trishydroxymethylaminomethane (TRIS) at pH 7.4. Weight loss was determined at various time points up to 28 days. Weight loss occurred using all buffer systems, with about 30-60% of the original (dry) sample weight remaining after 28 days. Gels with higher oxidized starch content exhibited greater weight loss. The weight loss results for chitosan/oxidized polysaccharide in PBS at pH 7.4 and 37° C. (without lysozyme) are shown in FIG. 6.

The oxidized starch-based gels appeared to degrade into a 'shell-like' material, whereas the oxidized cellulose-based gels appeared to remain as gels during degradation. The oxidized cellulose-based gels may be haemostatic.

The results in Examples 1-4 show that chitosan and oxidized polysaccharides may be combined to prepare injectable or sprayable formulations which quickly form strong protective gel layers in situ with inherent antimicrobial properties. The formulations were in each instance sprayable, antibacterial, biodegradable or bioresorbable and capable of serving as a scaffold for drug delivery.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

We claim:

1. An article of manufacture comprising a crosslinked hydrogel layer reacted from a fluid mixture containing chitosan and oxidized polysaccharide in amounts sufficient to form a protective gel layer in situ, the crosslinked hydrogel layer being in contact with and coating and conforming to the shape of cilia on a ciliated mucosal tissue in an ear, nasal cavity, sinus cavity or throat, the chitosan having a number average molecular weight before sterilization of at least about 50 kDa, and wherein the crosslinked hydrogel layer provides a protective gel layer that remains exposed to air or other nearby gases, reduces adhesions to anatomy, is biodegradable or bioresorbable without shedding large solid chunks and resists detachment or other disruption from such tissue until natural degradation or resorption of the protective gel layer takes place.

2. An article according to claim 1 wherein the crosslinked hydrogel layer is in contact with and coats and conforms to the shape of cilia on a ciliated mucosal nasal cavity tissue.

3. An article according to claim 1 wherein the crosslinked hydrogel layer is in contact with and coats and conforms to the shape of cilia on a ciliated mucosal throat tissue.

4. An article according to claim 1 wherein the chitosan is an unmodified chitosan or a chitosan salt.

5. An article according to claim 1 wherein the chitosan is a chitosan derivative.

6. An article according to claim 1 wherein the oxidized polysaccharide comprises oxidized starch.

7. An article according to claim 1 wherein the oxidized polysaccharide comprises oxidized cellulose.

8. An article according to claim 1 wherein the oxidized polysaccharide comprises oxidized chitin, oxidized chitosan, oxidized chondroitin sulfate, oxidized dextran, oxidized glycogen or oxidized hyaluronic acid.

9. An article according to claim 1 wherein the chitosan and oxidized polysaccharide are combined in a ratio of about 10:1 to about 1:20.

10. An article according to claim 1 wherein the chitosan and oxidized polysaccharide are combined in a ratio of about 3:1 to about 1:5.

11. An article according to claim 1 further comprising phosphate ions.

12. An article according to claim 1 wherein the chitosan is a low molecular weight material having a number average molecular weight before sterilization of about 50 to about 200 kDa.

13. An article according to claim 1 wherein the chitosan is a medium molecular weight material having a number average molecular weight of about 200 to about 500 kDa.

14. An article according to claim 1 wherein the chitosan is a high molecular weight material having a number average molecular weight greater than about 500 kDa.

15. An article according to claim 1 wherein the protective gel layer remains a gel during biodegradation or bioresorbtion.

16. An article according to claim 1 wherein the fluid mixture is sprayable before formation of the crosslinked hydrogel layer.

17. An article according to claim 1 wherein the protective gel layer has a residence time of one day to four weeks.

18. An article according to claim 1 wherein the protective gel layer includes available chitosan amine hydrogen atoms.

19. An article according to claim 1 wherein the fluid mixture consists essentially of chitosan, oxidized polysaccharide, a solvent selected from water and alcohols, and an optional buffering agent.

20. An article according to claim 1 wherein the crosslinked hydrogel layer is in contact with and coats and conforms to the shape of cilia on a ciliated mucosal sinus cavity tissue.

21. An article according to claim 1 wherein the fluid mixture contains chitosan and oxidized polysaccharide in a combined amount of about 1 to about 10 wt. % of the fluid mixture.

* * * * *